US00PP36553P3

(12) United States Plant Patent
Schoone

(10) Patent No.: US PP36,553 P3
(45) Date of Patent: Mar. 18, 2025

(54) ***PHALAENOPSIS* PLANT NAMED 'Flamboyance'**

(50) Latin Name: *Phalaenopsis hybrida*
Varietal Denomination: Flamboyance

(71) Applicant: FLORICULTURA B.V., Heemskerk (NL)

(72) Inventor: Rene Schoone, Assendelft (NL)

(73) Assignee: FLORICULTURA B.V., Heemskerk (NL)

( * ) Notice: Subject to any disclaimer, the term of this patent is extended or adjusted under 35 U.S.C. 154(b) by 0 days.

(21) Appl. No.: 18/735,105

(22) Filed: Jun. 5, 2024

(65) Prior Publication Data

US 2024/0415037 P1 Dec. 12, 2024

Related U.S. Application Data

(60) Provisional application No. 63/471,471, filed on Jun. 6, 2023.

(51) Int. Cl.
*A01H 5/02* (2018.01)
*A01H 6/62* (2018.01)

(52) U.S. Cl.
USPC ..... Plt./311
CPC ..... *A01H 6/62* (2018.05)

(58) Field of Classification Search
USPC ..... Plt./263.1, 311
See application file for complete search history.

(56) References Cited

U.S. PATENT DOCUMENTS

PP33,823 P3 * 1/2022 Schoone ..... Plt./311

* cited by examiner

*Primary Examiner* — Karen M Redden
(74) *Attorney, Agent, or Firm* — C. Anne Whealy

(57) ABSTRACT

A new and distinct cultivar of *Phalaenopsis* plant named 'Flamboyance', characterized by its upright plant habit; moderately vigorous growth habit; strong flowering stems; strong leaves; freely flowering habit with typically two inflorescences developing per plant, each inflorescence with numerous flowers; greenish yellow-colored flowers with conspicuous reticulated red-colored venation; and good postproduction longevity.

2 Drawing Sheets

Figure 1:
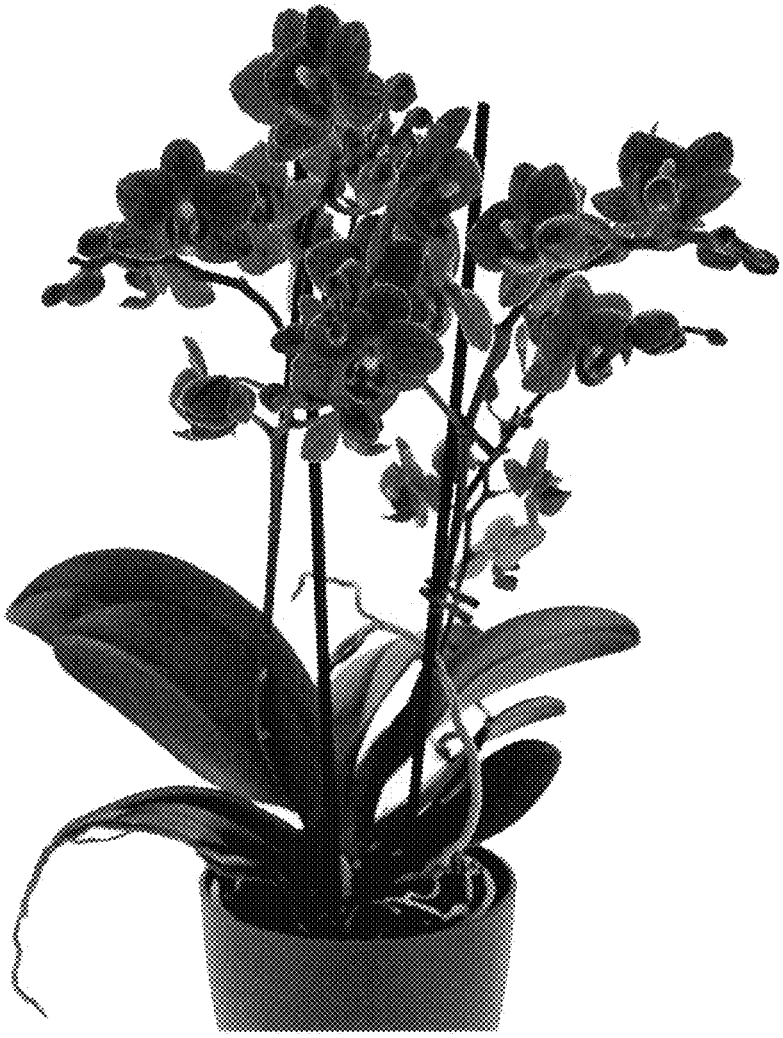

Botanical designation: *Phalaenopsis hybrida.*
Cultivar denomination: 'FLAMBOYANCE'.

STATEMENT REGARDING PRIOR DISCLOSURES BY INVENTOR AND APPLICANT/ASSIGNEE

A European Community Plant Breeder's Rights application for the instant plant was filed by the Applicant/Assignee of the instant application, Floricultura B.V. of Heemskerk, The Netherlands on Feb. 27, 2023, application number 2023/0516. Foreign priority is not claimed to this application.

The Inventor and Applicant/Assignee assert that no sales, offers for sale or public distribution of the instant plant occurred more than one year prior to the effective filing date of this application.

Any information about the claimed plant would have been obtained from a direct or indirect disclosure from the Inventor and/or Applicant/Assignee. Inventor and Applicant/Assignee claim a prior art exception under 35 U.S.C. 102(b)(1) for disclosures and/or sales prior to the filing date but less than one year prior to the effective filing date.

BACKGROUND OF THE INVENTION

The present invention relates to a new and distinct cultivar of *Phalaenopsis* plant, botanically known as *Phalaenopsis hybrida*, and hereinafter referred to by the name 'Flamboyance'.

The new *Phalaenopsis* plant is a product of a planned breeding program conducted by the Inventor in Assendelft and Heemskerk, The Netherlands. The objective of the breeding program is to develop new fast-growing and freely flowering *Phalaenopsis* plants with good leaf shape and flowers with unique and attractive patterns and coloration.

The new *Phalaenopsis* plant originated from a cross-pollination in January, 2013 in Assendelft, The Netherlands of *Phalaenopsis hybrida* 'Sogo Vivien', not patented, as the female, or seed, parent with *Phalaenopsis hybrida* 'Salu Peoker', not patented, as the male, or pollen, parent. The new *Phalaenopsis* plant was discovered and selected by the Inventor as a single flowering plant from within the progeny of the stated cross-pollination grown in a controlled greenhouse environment in Heemskerk, The Netherlands in December, 2019.

Asexual reproduction of the new *Phalaenopsis* plant by in vitro meristem propagation in a controlled environment in Assendelft, The Netherlands since January, 2021 has shown that the unique features of this new *Phalaenopsis* plant are stable and reproduced true to type in successive generations.

SUMMARY OF THE INVENTION

Plants of the new *Phalaenopsis* have not been observed under all possible combinations of environmental conditions and cultural practices. The phenotype may vary somewhat with variations in environmental conditions such as temperature and light intensity, without, however, any variance in genotype.

The following traits have been repeatedly observed and are determined to be the unique characteristics of 'Flamboyance'. These characteristics in combination distinguish 'Flamboyance' as a new and distinct *Phalaenopsis* plant:

1. Upright plant habit.
2. Moderately vigorous growth habit.
3. Strong flowering stems.
4. Strong leaves.
5. Freely flowering habit with typically two inflorescences developing per plant, each inflorescence with numerous flowers.
6. Greenish yellow-colored flowers with conspicuous reticulated red-colored venation.
7. Good postproduction longevity.

Plants of the new *Phalaenopsis* can be compared to plants of the female parent, 'Sogo Vivien'. Plants of the new *Phalaenopsis* differ primarily from plants of 'Sogo Vivien' in petal color as petals of plants of the new *Phalaenopsis* are greenish yellow-colored flowers with conspicuous reticulated red-colored venation whereas petals of plants of 'Sogo Vivien' are soft violet in color.

Plants of the new *Phalaenopsis* can be compared to plants of the male parent, 'Salu Peoker'. Plants of the new *Phalaenopsis* differ primarily from plants of 'Salu Peoker' in flower color as flowers of plants of the new *Phalaenopsis* are greenish yellow-colored flowers with conspicuous reticulated red-colored venation whereas flowers of plants of 'Salu Peoker' are greenish yellow in color and moderately to densely covered with spots, however without conspicuous venation.

Plants of the new *Phalaenopsis* can be compared to plants of *Phalaenopsis hybrida* 'Penny Lane', disclosed in U.S. Plant Pat. No. 27,230. In side-by-side comparisons, plants of the new *Phalaenopsis* differ primarily from plants of 'Penny Lane' in flower color as flowers of plants of the new *Phalaenopsis* are greenish yellow-colored flowers with conspicuous reticulated red-colored venation whereas flowers of plants of 'Penny Lane' are yellow in color with red purple-colored spots and stripes, however without conspicuous venation.

BRIEF DESCRIPTION OF THE PHOTOGRAPHS

The accompanying photographs illustrate the overall appearance of the new *Phalaenopsis* plant showing the colors as true as it is reasonably possible to obtain in colored reproductions of this type. Colors in the photographs may differ slightly from the color values cited in the detailed botanical description which accurately describe the colors of the new *Phalaenopsis* plant.

The photograph on the first sheet (FIG. 1) is a side perspective view of a typical flowering plant of 'Flamboyance' grown in a container.

Figure 2:
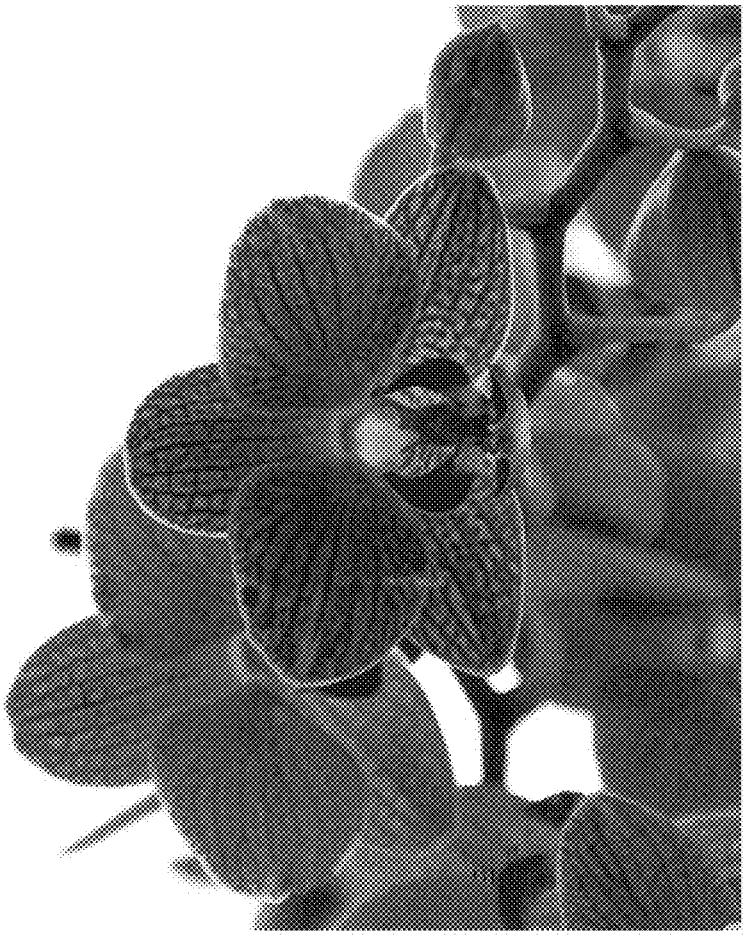

The photograph on the second sheet (FIG. 2) is a close-up view of a typical flowering plant of 'Flamboyance'.

DETAILED BOTANICAL DESCRIPTION

The aforementioned photographs and following observations and measurements describe plants grown during the winter in 12-cm containers in a glass-covered greenhouse in Heemskerk, The Netherlands and under cultural practices typically used in commercial *Phalaenopsis* production. Plants were 18 months old when the photographs and description were taken. During the first twelve months of production of the plants, day and night temperatures averaged 27° C. During the final six months of production of the plants, day temperatures ranged from 20° C. to 22° C. and night temperatures ranged from 18° C. to 20° C. During the production of the plants, light levels ranged from a minimum of 5 klux to a maximum of 10 klux. In the following description, color references are made to The Royal Horticultural Society Colour Chart, 2015 Edition, except where general terms of ordinary dictionary significance are used.

Botanical classification: *Phalaenopsis hybrida* 'Flamboyance'.

Parentage:

*Female, or seed, parent.*—*Phalaenopsis hybrida* 'Sogo Vivien', not patented.

*Male, or pollen, parent.*—*Phalaenopsis hybrida* 'Salu Peoker', not patented.

Propagation:

*Type.*—By in vitro meristem propagation.

*Time to initiate roots, summer and winter.*—About two weeks at temperatures about 28° C. to 30° C.

*Time to produce a rooted young plant, summer and winter.*—About 20 to 25 weeks at temperatures about 28° C. to 30° C.

*Root description.*—Thin, fibrous; typically light yellowish white in color; actual color of the roots is dependent on substrate composition, water quality, fertilizer, substrate temperature and age of roots.

*Rooting habit.*—Freely branching; medium density.

Plant description:

*Plant form and growth habit.*—Herbaceous epiphyte; upright plant habit with typically two inflorescences developing per plant, each inflorescence with numerous flowers; monopodial; moderately vigorous growth habit and moderate growth rate.

*Plant height, substrate level to top of foliar plane.*—About 12.8 cm.

*Plant height, substrate level to top of floral plane.*—About 27.9 cm.

*Plant diameter or spread.*—About 29.4 cm.

Leaf description:

*Arrangement and quantity.*—Distichous, simple; sessile; about six fully-developed leaves per plant.

*Length.*—About 15.9 cm.

*Width.*—About 7.2 cm.

*Aspect.*—Semi-erect to somewhat outwardly arching.

*Shape.*—Broadly elliptic; slightly carinate; apex moderately reflexed.

*Apex.*—Unequal acute.

*Base.*—Sheathing. Sheath length: About 1.5 cm. Sheath width: About 1.3 cm. Sheath color, upper and lower surfaces: Close to 143C.

*Margin.*—Entire.

*Texture and luster, upper and lower surfaces.*—Smooth, glabrous; slightly glossy.

*Venation pattern.*—Camptodromous.

*Color.*—Developing leaves, upper surface: Close to NN137A. Developing leaves, lower surface: Close to 137C. Fully expanded leaves, upper surface: Close to NN137B; venation, close to 139A. Fully expanded leaves, lower surface: Close to 146B; venation, close to 137B.

Inflorescence description:

*Appearance and flowering habit.*—Showy zygomorphic flowers arranged on axillary simple or branched racemes; typically two inflorescences develop per plant; each inflorescence with about 35 flowers;

flowers face outwardly on outwardly arching inflorescences supported by upright peduncles; flowers with three petals, two lateral petals and one center petal transformed into a labellum and three sepals.

*Fragrance*.—None detected.

*Time to flower*.—Plants begin flowering about six months after planting; plants flower naturally during the winter into the spring.

*Flower longevity*.—Long flowering period, individual flowers maintain good substance for about six weeks on the plant; flowers not persistent.

*Inflorescence length* (*lowermost flower to inflorescence apex*).—About 23.9 cm.

*Inflorescence width*.—About 16.3 cm.

*Flower buds, about one week before opening*.—Height: About 1.4 cm. Diameter: About 1.2 cm. Shape: Broadly ovate. Color: Close to a blend of N144C and 146D; towards the apex, tinged with close to 152B; towards the base, close to N144D.

*Flower size*.—About 3.9 cm (vertical) by 4.3 cm (horizontal).

*Flower depth*.—About 2.6 cm.

*Petals, quantity and arrangement*.—Three, two lateral petals and one center petal transformed into a labellum.

*Lateral petals*.—Length: About 2.1 cm. Width: About 2.1 cm. Shape: Broadly ovate to roughly deltoid-ovate. Apex: Obtuse. Margin: Entire; not undulate. Texture and luster, upper surface: Smooth, glabrous; moderately velvety; matte. Texture and luster, lower surface: Smooth, glabrous; slightly velvety; matte. Color: When opening, upper surface: Close to 152D; towards the base, tinged with close to 173B; conspicuous reticulated venation, close to 183A; narrow marginal edges, close to 151D. When opening, lower surface: Close to 151B; towards the apex and margins, strongly tinged with close to 164B; conspicuous reticulated venation, close to 178B and 178C; narrow marginal edges, close to 151D. Fully opened, upper surface: Close to 152D and 153A; conspicuous reticulated venation, close to 181A; narrow marginal edges, close to 151D. Fully opened, lower surface: Close to 151B and 151C; towards the apex and margins, strongly tinged with close to 164C; conspicuous reticulated venation, close to 178C and 178D; narrow marginal edges, close to 151D.

*Labella*.—Appearance: Three-parted with two lateral lobes and a central lobe. Length, lateral lobes: About 1.1 cm. Width, lateral lobes: About 5 mm. Length, central lobe: About 1.3 cm. Width, central lobe: About 0.2 cm to 1.4 cm. Shape, lateral lobes: Narrowly obovate. Shape, central lobe: Ovate; moderately concave. Apex, lateral lobes: Obtuse. Apex, central lobe: Shallowly emarginate. Margins, lateral and central lobes: Entire. Texture and luster, lateral and central lobes, upper and lower surfaces: Smooth, glabrous, moderately velvety; matte. Callosities: Located at the base of the labellum and attachment point of the lateral petals; about 3 mm in length, about 3 mm in width and about 2 mm in height. Color: When opening, upper surface: Lateral lobes: Close to 185A; towards the apex, close to 64A; towards the base, close to 10D and at the base, close to 12A. Central lobe: Close to a blend of 181A and 183B; towards the apex, close to 64A and at the apex, close to 76C; at the base, close to 181A. When opening, lower surface: Lateral lobes: Close to 64A and 64B; towards the base, close to 165D. Central lobe: Close to 184B; towards the apex, close to 64A; towards the base, close to 151A and 151B and at the base, close to 160D; central band, close to 75B. Fully opened, upper surface: Lateral lobes: Close to 185A; towards the apex, close to 64A; towards the base, close to 10D and at the base, close to 12A. Central lobe: Close to 181A; towards the apex, close to 60C and at the apex, close to 76C. Fully opened, lower surface: Lateral lobes: Close to 64A and 64B; towards the base, close to 165D. Central lobe: Close to 184C; towards the apex, close to 64B; towards the base, close to 160B and at the base, close to 160D; central band, close to 75B. Callosities, when developing and fully developed: Close to 15A; toward the apex and inner surface, close to 180A and 180B.

*Sepals*.—Quantity and arrangement: Three, one upper dorsal sepal and two lower lateral sepals. Length, dorsal sepal: About 2.3 cm. Width, dorsal sepal: About 1.6 cm. Length, lateral sepals: About 2.3 cm. Width, lateral sepals: About 1.7 cm. Shape, dorsal sepal: Elliptic. Shape, lateral sepals: Broadly ovate. Apex, dorsal sepal: Obtuse to shallowly retuse. Apex, lateral sepals: Broadly and bluntly acute. Base, dorsal and lateral sepals: Truncate. Margins, dorsal and lateral sepals: Entire; not undulate. Texture and luster, dorsal and lateral sepals, upper and lower surfaces: Smooth, glabrous; moderately velvety; matte. Color, dorsal sepal: When opening, upper surface: Close to 152D; towards the base, close to 173B; conspicuous reticulated venation, close to 183A and 183B; narrow marginal edges, close to 151D. When opening, lower surface: Close to 151A; towards the apex, close to 152D; venation, close to N184A. Fully opened, upper surface: Close to 152D; towards the base, tinged with close to 173C and at the base, close to 195D; conspicuous reticulated venation, close to 184A and 184B; narrow marginal edges, close to 151C. Fully opened, lower surface: Close to 160A and 160B; towards the apex and margins, tinged with close to 164B, 164C and 165C; narrow marginal edges, close to 151D. Color, lateral sepals: When opening, upper surface: Close to 151B; conspicuous reticulated venation, close to 183A and 183B; narrow marginal edges, close to 151B. When opening, lower surface: Close to 151A; towards the apex, close to 152D; venation, close to N184A. Fully opened, upper surface: Close to a blend of 151D and 154C; towards the base, tinged with close to 151C; conspicuous reticulated venation, close to 184B and 184C; narrow marginal edges, close to 151C. Fully opened, lower surface: Close to 160A; towards the apex and margins, slightly tinged with close to 164B and 164C; narrow marginal edges, close to 151D.

*Peduncles*.—Length: About 31.9 cm. Diameter: About 4.5 mm. Strength: Strong. Aspect: Upright to outwardly arching. Texture and luster: Smooth, glabrous; matte. Color: Close to NN137D covered with fine blotches and spots, close to 143A.

*Pedicels*.—Length: About 2.5 cm. Diameter: About 2 mm. Strength: Moderately strong. Aspect: About 70° from peduncle axis. Texture and luster: Smooth, glabrous; matte. Color: Close to 144C; proximally, close to 144A; distally, close to 145C.

*Reproductive organs*.—Androecium: Column length: About 9 mm. Column width: About 5 mm. Column color: Close to N75B and N75C; distally, close to NN155A; center, tinged with close to 72B. Pollinia quantity: Two. Pollinia diameter (per two pollinia): About 2 mm. Pollinia color: Close to 24A. Gynoecium: Stigma length: About 3 mm. Stigma width: About 4 mm. Stigma shape: Reniform. Stigma color: Close to 157D. Ovary length: About 8 mm. Ovary diameter: About 1 mm. Ovary color: Close to 149C.

Seeds and fruits: To date, seed and fruit development have not been observed on plants of the new *Phalaenopsis*.

Pathogen & pest resistance: To date, plants of the new *Phalaenopsis* have not been shown to be resistant to pathogens and pests common to *Phalaenopsis* plants.

Temperature tolerance: Plants of the new *Phalaenopsis* have been observed to tolerate high temperatures about 40° C. and are suitable for USDA Hardiness Zones 10 to 12.

It is claimed:

1. A new and distinct *Phalaenopsis* plant named 'Flamboyance' as herein illustrated and described.

* * * * *